(12) United States Patent
Klee et al.

(10) Patent No.: US 9,248,005 B2
(45) Date of Patent: Feb. 2, 2016

(54) DENTAL OBTURATOR POINT

(75) Inventors: Joachim E. Klee, Radolfzell (DE);
Christoph Weber, Constance (DE);
Frank Pfefferkorn, Duchtlingen (DE);
Tim Hornung, Constance (DE); Anja Glaner, Constance (DE)

(73) Assignee: Dentsply DeTrey GmbH, Constance (DE)

( * ) Notice: Subject to any disclaimer, the term of this patent is extended or adjusted under 35 U.S.C. 154(b) by 787 days.

(21) Appl. No.: 13/382,768

(22) PCT Filed: Jul. 6, 2010

(86) PCT No.: PCT/EP2010/004121
§ 371 (c)(1),
(2), (4) Date: Jan. 26, 2012

(87) PCT Pub. No.: WO2011/003592
PCT Pub. Date: Jan. 13, 2011

(65) Prior Publication Data
US 2012/0135377 A1    May 31, 2012

(30) Foreign Application Priority Data
Jul. 8, 2009  (EP) .................... 09008925

(51) Int. Cl.
*A61C 5/04*    (2006.01)
*A61C 5/02*    (2006.01)
*A61K 6/06*    (2006.01)
*A61K 6/09*    (2006.01)
*A61K 6/00*    (2006.01)

(52) U.S. Cl.
CPC . *A61C 5/02* (2013.01); *A61C 5/025* (2013.01); *A61C 5/04* (2013.01); *A61K 6/0038* (2013.01); *A61K 6/06* (2013.01); *A61K 6/0681* (2013.01); *A61K 6/0032* (2013.01); *A61K 6/09* (2013.01)

(58) Field of Classification Search
CPC ...... A61K 6/0038; A61K 6/0032; A61K 6/09
See application file for complete search history.

(56) References Cited

U.S. PATENT DOCUMENTS

| 4,425,094 | A  | * | 1/1984  | Tateosian et al. ......... 433/228.1 |
| 5,118,297 | A  |   | 6/1992  | Johnson |
| 8,088,838 | B2 |   | 1/2012  | Hsieh et al. |
| 2004/0115589 | A1 |   | 6/2004  | Karmaker et al. |
| 2008/0274439 | A1 | * | 11/2008 | Gutzner et al. ............... 433/102 |

FOREIGN PATENT DOCUMENTS

| EP | 1688101    | A1 |   | 8/2006 |          |
| EP | 1911433    | A1 | * | 4/2008 | ............... A61K 6/00 |
| WO | 2006082078 | A1 |   | 8/2006 |          |
| WO | 2008046557 | A1 |   | 4/2008 |          |

* cited by examiner

*Primary Examiner* — Michael Pepitone
(74) *Attorney, Agent, or Firm* — McNees Wallace & Nurick LLC

(57) ABSTRACT

Dental obturator point having an obturation body containing a composite material comprising (a) a polymer and b) a particulate filler, whereby the obturation body has a radio opacity of at least 3 mm/mm Al, characterized in that the composite material has (i) a tensile strength of from 5 to 70 MPA1 (ii) a flexural strength of from 5 to 90 MPA, (iii) a flexural module of from 0.1 to 2.5 GPa, and which has (iv) a 300 rpm drilling coefficient at 37° C. in the range of from −1 to 7.00.

12 Claims, 2 Drawing Sheets

DENTAL OBTURATOR POINT

CROSS-REFERENCE TO RELATED APPLICATIONS

This application is the National Stage of International Application No. PCT/EP2010/004121, filed Jul. 6, 2010, which International Application claims priority to currently pending European Patent Application EP 09008925.1 filed Jul. 8, 2009.

FIELD OF THE INVENTION

The present invention relates to a dental obturator point having excellent mechanical properties and at the same time superior properties during treatment and also retreatment of a dental root canal having been obturated with the dental obturator point of the present invention. The dental obturator point of the invention has superior dimensional stability, in particular in the longitudinal direction.

BACKGROUND OF THE INVENTION

Dental obturator points are known (WO2006/082078). Dental obturator points are used by the dental practitioner in endodontic therapy to fill a prepared root canal. Given the small dimensions of the root canal and the fact that root canals are frequently not straight, but shaped with turns and screw-like portions, any obturator point used for dental purposes must provide a combination of high strength and flexibility.

Moreover, given that radio opacity of the dental obturator point is essential in subsequent diagnostic methods, obturator points are required to contain significant amounts of radio opaque material such as specific inorganic fillers.

Moreover, during retreatment of a dental root canal which had previously been filled with a dental obturator point, it is necessary to eliminate the dental obturator point completely from the dental root canal by using conventional dental instruments.

Moreover, dimensional stability of the dental obturator point is essential during storage given that dental obturator points are distributed in standardized sizes. Dimensional stability of the dental obturator point in the root canal is also important for the success of the root canal therapy.

Gutta percha is conventionally the predominant material used to obturate a root canal after it has undergone endodontic therapy. The physical and chemical properties of gutta percha, including inertness and biocompatibility, melting point, ductility and malleability, and excellent retreatment properties are the reason that dental obturator points are usually made of gutta percha filled with about 70 percent by weight of zinc oxide. However, the mechanical properties of the gutta percha obturation points are considered to be unsatisfactory.

U.S. Pat. No. 4,425,094 discloses an endodontic points comprising hydrophilic, polymeric compositions, which are swellable when placed into a prepared root canal. The hydrophilic, polymeric composition may be a hydrophilic, polymeric urethane. However, the mechanical properties of the endodontic points are still unsatisfactory.

U.S. Pat. No. 5,118,297 discloses a dental obturator point having an obturation body of a plastic material such as UDEL polysulfone MG-11 (AMOCO Performance Products, Ine) or Vectra VC-3 (Hoechst Celanese Corp.) optionally containing powdered tungsten as an inorganic particulate filler.

The dental obturator point of U.S. Pat. No. 5,118,297 is problematic in that the material suggested for the obturation body is excessively stiff. Moreover, the plastic material suggested cannot be readily eliminated from the dental root canal in case of a retreatment of the dental root canal.

WO-A 2008046557 discloses a dental obturator point having an obturation body of a material comprising (a) a polymer blend comprising (a1) 5 to 95 wt % based on the total amount of the polymer blend of a thermoplastic epoxide amine addition polymer, and (a2) 95 to 5 wt % based on the total blend of a high performance polymer; and (b) a particulate filler; whereby the obturation body has a radio opacity of at least 3 mm/mm Al. Although the obturator point of WO-A 2008046557 provides improved mechanical properties with regard to strength and flexibility, the properties of the obturator point with regard to a retreatment of a dental root canal still need improvement.

EP 1 911 433 discloses a dental obturator point comprising a polymer blend of a thermoplastic epoxide amine addition polymer and a high performance polymer, and a filler. Although the mechanical properties of the dental obturator point are excellent, a retreatment of a root canal treated with the dental obturator point is hardly possible, cf. Comparative Example 1.

It is therefore an object of the present invention to provide a dental obturator point having an obturation body with high strength, excellent flexibility, and high radio opacity, whereby the dental obturator point may be easily produced, while at the same time the dental obturator point may be readily eliminated from the dental root canal by using conventional dental instruments used for the treatment of a root canal.

Moreover, the dental obturator points should preferably fulfill the requirements of ISO 6877, especially with regard to the brittleness test and the required radio-opacity of at least 6 compared to 1 mm aluminium.

SUMMARY OF THE INVENTION

The present invention provides a dental obturator point having an obturation body containing a composite material comprising
(a) a polymer and
(b) a particulate filler,
whereby the obturation body has a radio opacity of at least 3 mm/mm Al, characterized in that the composite material has
(i) a tensile strength of from 5 to 70 MPa,
(ii) a flexural strength of from 5 to 90 MPa,
(iii) a flexural module of from 0.1 to 2.5 GPa, and which has at the same time
(iv) a 300 rpm drilling coefficient at 37° C. in the range of from −1 to 7.00.

The dental obturator point preferably has a dimensional stability in the longuitudinal direction of not more than 0.25% per mm total length of the obturator point after storage for 5 days at 37° C. and 90% relative humidity.

Furthermore, the present invention provides a method for producing a dental obturator point, which comprises the following steps:
(1) providing a thermoplastic composite material comprising a polymer and a particulate filler, and
(2) molding the composite material to provide a dental obturator point having an obturation body having a radio opacity of at least 3 mm/mm Al,
characterized in that the composite material has
(i) a tensile strength of from 5 to 70 MPa,
(ii) a flexural strength of from 5 to 90 MPa,
(iii) a flexural module of from 0.1 to 2.5 GPa, and which has (iv) a 300 rpm drilling coefficient at 37° C. in the range of from −1 to 7.00.

The dental obturator point may comprise a tapered obturating body integrally connected at the distal end of a functional portion, whereby the functional portion comprises
(1) a neck portion adjacent to the obturating body, and
(2) a handle portion.

Furthermore, the present invention provides a system comprising multiple dental obturator points according to the present invention.

DETAILED DESCRIPTION OF THE INVENTION

Figure 1:
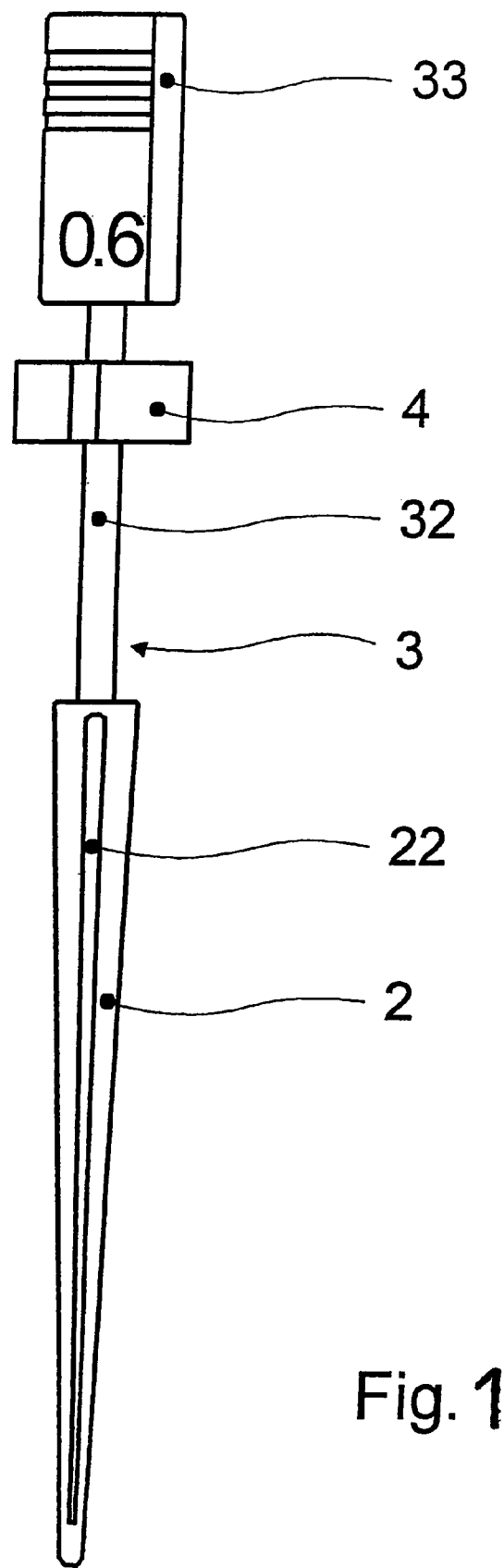
FIG. 1 shows a preferred dental obturator point according to the invention.

The dental obturator point according to the invention has an obturation body. The size and shape of the obturation body is adapted to the typical sizes and shapes of a root canal and the sizes of files used for the preparation of the root canal.

The dental obturator point preferably has a dimensional stability in the longuitudinal direction of not more than 0.25% per mm total length of the obturator point after storage for 5 days at 37° C. and 90% relative humidity. More preferably, the dimensional stability in the longuitudinal direction of the dental obturator point in the longuitudinal direction is not more than 0.20%, still more preferably 0.15% and still more preferably 0.12% per mm total length of the obturator point after storage for 5 days at 37° C. and 90% relative humidity.

Moreover, the dental obturator point preferably has a dimensional stability in the longuitudinal direction of not more than 0.40% per mm total length of the obturator point after storage for 5 days at 50° C. and 90% relative humidity. More preferably, the dimensional stability in the longuitudinal direction of the dental obturator point in the longuitudinal direction is not more than 0.35%, still more preferably 0.33% and still more preferably 0.30% per mm total length of the obturator point after storage for 5 days at 37° C. and 90% relative humidity.

In view of the variation of the shapes and sizes of root canals and the sizes of files used for the preparation of the root canal, dental obturator points may be combined in a kit of parts wherein one or more dental obturator points with an obturation body of a specific size and shape are combined with one or more obturator points with an obturation body of a different specific size and shape, and files of a corresponding size. Preferably, the contour of the distal portion of the obturation body corresponds to the contour of the distal portion of the file used for the final preparation of the root canal.

The dental obturator point according to the invention may comprise further portions such as handle portions or neck portions integrally attached to the obturation body. The material of any optional further portions may be the same or different as the material of the obturation body. The obturation body has a radio opacity of at least 3 mm/mm Al. Preferably, the radio opacity is at least 5 mm/mmAl, more preferably at least 6 mm/mmAl.

The obturation body contains a composite material. In a preferred embodiment, the obturation body consists of a composite material. A composite material is made from two or more constituent materials with significantly different physical or chemical properties which remain separate and distinct on a macroscopic level within the finished structure. The composite material of the present invention comprises polymer and particulate filler.

The composite material of the obturation body is characterized by a set of mechanical properties. Specifically, the composite material represents a specific combination of tensile strength, flexural strength and flexural module. Moreover, as an essential feature of the present invention, the composite material is required to fulfill at the same time a specific parameter defined as a 300 rpm drilling coefficient at 37° C. Finally, the composite material of the obturation body provides a high dimensional stability in the longuitudinal direction.

The present invention is based on the recognition that retreatment properties of an obturation body which has been installed in a dental root canal do not correlate with usual mechanical properties. Therefore, it is not possible to show consistent trends in the retreatment properties when changing usual mechanical properties such as tensile strength, flexural strength or flexural module. In particular, a number of different properties of the composite material appear to have an influence on the complete removal of the obturation body from the root canal during retreatment.

In fact, retreatment of a dental root canal represents a complex process wherein the material of the obturation body is removed in a series of mechanical steps which aim at separating the obturation body from the wall of the root canal, the comminution of the obturation body and the removal of the comminuted obturation body from the root canal.

When using conventional instruments for retreatment of the root canal, separation, comminution and removal occur simultaneously whereby mechanical properties including tensile strength, flexural strength or flexural module appear to exert an opposing influence on separation, comminution and removal responsible for the progress of the retreatment. Therefore, it is not possible to describe retreatment properties with a set of usual parameters for mechanical properties.

Surprisingly, it is possible to map the influence of the properties of an obturator point on the retreatment process to a single parameter and to identify a class of obturation bodies which have at the same time excellent properties with regard to obturation and with regard to retreatment. By selecting from this class of obturation bodies a further class which has high dimensional stability in the longuitudinal direction, a superior obturation point may be provided.

Specifically, the composite material is required to fulfil the specific 300 rpm drilling coefficient at 37° C. as defined by the present invention. It was found that the retreatment properties correlate with the following formula (I):

$$\text{Drilling Coefficient} = (D_x - D_{GP})/D_{GP}$$

wherein
$D = \text{Load} \times \text{Time}^2/\text{Thickness}^2 \text{ gs}^2/\text{mm}^2$, and
x refers to a composite material and GP to a conventional gutta percha material (gutta percha/zinc oxide 30/70% by weight).

Therefore, the composite material used according to the invention has
(i) a tensile strength of from 5 to 70 MPa,
(ii) a flexural strength of from 5 to 90 MPa,
(iii) a flexural module of from 0.1 to 2.5 GPa, and which has
(iv) a 300 rpm drilling coefficient at 37° C. in the range of from −1 to 7.00.

The dimensional stability indicates the change in length of the dental obturator point of an initial length after production, e.g. by injection molding, per mm of the length of the obturator point. Accordingly, the dimensional stability may be calculated according to the following formula:

$$((\text{length after production (mm)})-(\text{length after storage (mm)}))\times 100/(\text{length after production (mm)})^2$$

Therefore, the dental obturator point preferably has a dimensional stability in the longituudinal direction of not more than 0.25% per mm total length of the obturator point after storage for 5 days at 37° C. and 90% relative humidity.

The parameters (i) to (iii) are important with regard to the obturation properties of the dental obturation point of the invention whereas parameter (iv) determines the retreatment properties of the dental obturation point of the invention.

The dimensional stability in the longituudinal direction determines the storage and handling properties of the dental obturator point.

Tensile strength is the stress where necking of the composite material of the dental obturation point begins and represents the maximum of the stress-strain curve. The tensile strength of the composite material is adjusted to from 5 to 70 MPA, preferably to from 10 to 60 MPA. The tensile strength is determined according to ISO 527-1: 1993. In case the composite material has a tensile strength which outside this range, the obturation properties are likely to deteriorate.

Flexural strength is reflects the highest stress experienced within the composite material of the dental obturation point at its moment of rupture. The flexural strength of the composite material is adjusted to from 5 to 90 MPa, preferably to from 10 to 80 MPA. The flexural strength may be determined according to DIN EN ISO 178: 2006-04 (D).

The flexural module describes the tendency of the composite material of the dental obturation point to be deformed elastically when a force is applied to it. The flexural module of the composite material is in adjusted of from 0.1 to 2.5 GPa, preferably of from 0.5 to 50 GPa. The flexural module may be determined according to DIN EN ISO 178: 2006-04 (D).

300 rpm drilling coefficient at 37° C. reflects the retreatment properties of the composite material of the dental obturation point. Retreatment properties are acceptable according to the present invention if the 300 rpm drilling coefficient at 37° C. is adjusted in the range of from −1 to 7, preferably in the range of from −0.9 to 5, more preferably −0.6 to 4.

Figure 2:
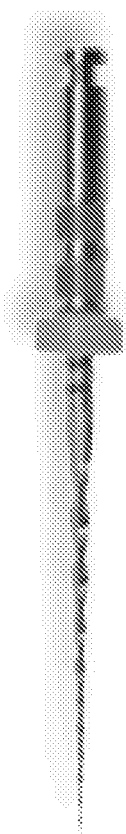
FIG. 2 shows a Mtwo retreatment file (red) (size/taper 025/0.05) available from VDW GmbH, which is used for determining the 300 rpm drilling coefficient at 37° C. according to the present invention.

The 300 rpm drilling coefficient at 37° C. may be measured as follows. A test specimen having the dimensions (L×W×T) of about 10 mm×10 mm×3 mm is prepared by using a composite material. The thickness of the final test specimen is subsequently measured with high precision and recorded for the calculation of the parameter. The test specimen is attached to an isothermal support kept at 37° C. for securing and holding the test specimen into place. After temperature equilibration of the test specimen, the time is measured for drilling a hole through the test specimen by using a dental drill operating at 300 revolutions per minute, whereby the drill is under a defined load of from 100 to 500 g. The drill to be used for the measurement is a conventional dental file for the treatment of a dental root canal. In general, the parameter shows a limited dependence on the specific type of file used as long as the dental file is used in the cutting mode. Preferably, a NiTi file for coronal filling removal is used. Specifically, an Mtwo retreatment file (red) (size/taper 025/0.05) available from VDW GmbH, is used which is a NiTi file as shown in FIG. 2. The load, time, and thickness are recorded for a material of interest and gutta percha and the 300 rpm drilling coefficient at 37° C. is calculated according to formula (I).

The composite material of the obturation body of the dental obturator point according to the invention comprises a polymer. The polymer may be a single type of polymer or a blend of two or more different types of polymers. A polymer for use in the composite material of the present invention may be selected from polyacrylates/methacrylates, polyurethanes, polyalkylenes such as polypropylenes and polyethylenes, polyamides, polyesters, fluoropolymers, polyphosphazenes, polyanhydrides, polysulfides, polyethers, epoxies, polycarbonates, polystyrenes, polybutadienes, polyisoprenes, polyphenylene oxides, silicone rubbers, polyglycolides, polylactides, polycaprolactones, polyamides, polyesteramides, polyorthoesters, polydioxanones, polyacetals, polyketals, polyorthocarbonates, polyhydroxybutyrates, polyhydroxyvalerates, polyalkylene oxalates, polyethylene oxides, polyalkylene succinates, poly (malic acid) polymers, polymaleic anhydrides, poly (methylvinyl)ethers, poly (amino acids), chitin, chitosan, polyamides, polyesters, polyimides, polyolefins, polyarylates, styrenes, polyurethanes, vinyl esters or epoxy-based materials, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates, polyethylene glycol dimethacrylate, triethylene glycol dimethacrylate, urethane dimethacrylate, hexane diol dimethacrylate, and polycarbonate dimethacrylate (hereinafter abbreviated "PCDMA"), and copolymers, terpolymers, or combinations or mixtures thereof. Preferably, polyurethanes, fluoropolymers and polyalkylenes are used in the present invention.

The polymer to be used in the present invention preferably has a glass transition temperature Tg of at least 40° C. more preferably at least 45° C.

A polyurethane may be an aliphatic polyurethane or an aromatic polyurethane. A polyurethane may be a reaction product of diisocyanates, diols and optionally chain extenders, whereby hard and soft domains of the polymer chain are formed, wherein the diisocyanate and extender make up the hard domains and the diol makes up the soft domain. Preferably, the Shore A hardness of suitable polyurethanes is in the range of from 55 A to 90 A, preferably 60 A to 80 A.

Preferably, the polyurethane is a polymer comprising the following repeating units:

wherein $R^1$ represents a straight or branched C1-C8 alkylene group and $R^2$ represents an aromatic moiety. Preferably, $R^1$ represents a straight or branched C2-C6 alkylene group. Preferably, the aromatic moiety for $R^2$ is derived from 4,4'-methylenediphenyl diisocyanate (MDI), 2,4-toluenediisocyanate (TDI) or 1,5-naphtalene diisocyanate (NDI). Tecothane® and Tecoplast® resins are examples for commercially available polyurethanes using methylene diisocyanate (MDI) for providing an aromatic moiety $R^2$. Examples for suitable chain extenders are polytetramethylene ether glycol (PTMEG) and 1,4 butanediol.

A preferred polymer with regard to dimensional stability is Tecothane®.

Alternatively, the polyurethane may be a resin manufactured using an aliphatic compound for providing a moiety $R^2$, such as hydrogenated methylene diisocyanate (HMDI). Examples for commercially available materials are Tecoflex®, Tecophilic® and Carbothane®.

The composite material of the obturation body of the dental obturator point according to the invention comprises a filler.

The composite may comprise at least 20 wt. % based on the entire composition of a particulate filler, preferably the filler content is in the range of from 25 to 70 wt.-%, more preferably 30 to 50 wt.-%.

Furthermore, the composite may comprise at least 1 vol. % based on the entire composition of a particulate filler, preferably the filler content is in the range of from 2 to 40 vol.-%, more preferably 3 to 20 vol.-%.

The filler may include inorganic and organic particulates and fibrous including tungsten, bismuth compounds such as BiOCl, silica, silicate glass, quartz, zinc oxide, barium sulfate, barium silicate, strontium silicate, barium borosilicate, strontium borosilicate, borosilicate, lithium silicate, amorphous silica, calcium phosphate and alumina, zirconia, tin oxide, and titania. Preferably, the fillers act as radiopaque/high refractive index materials, such as a metal like W or Bi, or $La_2O_3$, $ZrO_2$, $BiPO_4$, $CaWO_4$, $BaWO_4$, $SrF_2$, $Bi_2O_3$.

The filler is incorporated so as to provide a radio-opacity of at least 3 mm/mm Al, preferably at least 5 to 7 mm/mm Al, most preferably at least 6 mm/mm Al.

The dental obturator point according to the invention may contain additives such as a stabilizer, a plasticizer or a bioactive substance. The bioactive material may include any substance or metabolic precursor thereof, which is capable of promoting growth and survival of cells, tissues, and bone. Suitable bone growth promoting substances include bioglass, calcium phosphate, Portland cement, hydroxyapatite, tricalcium phosphate, a di- or polyphosphonic acid, a sodium fluoride preparation, calcium hydroxide, other suitable calcium-containing compounds. The filling material may include additives typical in the dental field such as plasticizing, antibiotic, cariostatic, antibacterial, or other anti-inflammatory, biologically active or therapeutic materials.

The dental obturator point according to a preferred embodiment comprising a tapered obturating body integrally connected at the distal end of a functional portion, is characterized in that the functional portion comprises
(1) a neck portion adjacent to the obturating body, and
(2) a handle portion.

The preferred dental obturator point also improves handling properties and enhances the precision of the root canal obturation. The handle portion of the dental obturator point may be firmly gripped by the finger of the operator or indirectly with an instrument like tweezers. By applying pressure, the tapered obturating body is pushed into its final position. The handle portion is preferably flat and can be easily bypassed by an instrument used to cut back the point at the end of the procedure. A flat surface preferably provided at the handle portion also offers space for imprints to identify size and taper of the point.

The neck portion of the preferred dental obturator point connects the handle portion with the intra-canicular tapered obturating body. The neck portion may have a reduced diameter in comparison to the tapered obturating body which facilitates the cut back of the point at the end of the procedure. In the neck portion a silicon stop may be mounted which helps to control that the tapered obturating body reaches its final position that is identical to the length of the root canal preparation instrument used.

The intra-canicular tapered obturating body is preferably shaped like the corresponding root canal instruments. It may exhibit an axial groove which allows excess sealant to escape in a coronal direction. The surface of the intra-canicular tapered obturating body may have a micro structure which allows an easy and complete wetting of the surface of the point with the root canal sealant and which also improves the bond strength between a root canal point and a root canal sealant.

As shown in FIG. 1, the dental obturator point comprises a tapered obturating body 2 integrally connected at the distal end of a functional portion 3, whereby the functional portion 3 comprises a neck portion 32 adjacent to the obturating body 2, and a handle portion 33. The handle portion 33 has a flat shape thereby providing a surface for an imprint. Moreover, the flat shape of the handle portion reduces any undesired visual obstruction. The neck portion 32 is provided with a stopper means 4 such as a silicon stopper. The stopper means may be color coded so as to indicate the type or size of the tapered obturating body 2. The neck portion 32 has a reduced diameter as compared to the tapered obturating body 2, thereby reducing any undesired visual obstruction. Moreover, the reduced diameter of the neck portion 32 improves the cutting efficiency when the functional portion is removed after the tapered obturating body 2 has been correctly placed in the root canal during therapy. The tapered obturating body 2 may be adapted to the shape of a root canal instrument used for the preparation of the root canal. Moreover, the tapered obturating body 2 may comprise one or more elongated channel portions 22 for draining excess sealant In a preferred embodiment, the tapered obturating body of the dental obturator point according to the invention has a roughened or otherwise mechanically or chemically modified surface structure for enhancing wetting and adhesion of the endodontic sealant. The tapered obturating body may comprise one or more elongated channel portions for draining excess sealant.

In a preferred embodiment, the handle portion has a non-circular cross section. The neck portion may have a cylindrical cross section. Moreover, it is preferred that the neck portion has a diameter which is the same or smaller than the diameter of the maximum diameter of the obturating body.

The dental obturator point according to the invention may further comprise a stopper means slidably provided at the neck portion.

The dental obturator point according to the invention is obtainable by a molding method. The molding method for preparing a dental obturator point according to the present invention is not specifically limited. Any molding method conventionally used for shaping products of the required size may be employed such as such as injection moulding, a thermal pressure forming process, and a casting process wherein a composition is polymerized in a mould.

In accordance with one method of manufacture herein, the dental obturator point is manufactured by die processes, autoclave molding, resin injection molding (RIM), sheet, dough and bulk molding, press molding, injection molding, reaction injection molding, resin transfer molding (RTM), compression molding, open molding, hand rolling, dipping and rolling, pressing, extrusion, pultrusion and filament winding. A preferred molding technique is injection molding. Alternatively, a rod shaped material may be manufactured and thereafter shaped by grinding, cutting, milling or the like into the desired shape and size.

The dental obturator point may be provided in an opaque tooth color for reasons of esthetics. The dental obturator point may include an appropriate amount of radiopaque material such as tungsten, titanium oxide, bismuth oxychloride, barium sulfate, and similar materials to insure X-ray documentation which may be added to the post material during manufacture thereof.

The invention will now be further illustrated based on the following Examples and Comparative Examples.

Example 1

Composite materials were prepared according to the compositions shown in Table 1 and the drilling coefficient was determined. Accordingly, a test specimen having the dimensions (L×W×T) of about 10 mm×10 mm×3 mm was prepared by using a composite material as identified in Table 1. The thickness of the final test specimen was subsequently measured with high precision and recorded for the calculation of the parameter. The test specimen was attached to an isothermal support kept at 37° C. for securing and holding the test specimen into place. After temperature equilibration of the test specimen, the time is measured for drilling a hole through the test specimen by using a Mtwo retreatment file (red) (size/taper 025/0.05) available from VDW GmbH, operated at 300 revolutions per minute, whereby the drill was under a defined load of from 100 to 500 g. The load, time, and thickness are recorded for a material of interest and gutta percha and the 300 rpm drilling coefficient at 37° C. is calculated according to formula (I).

| Blend # | LOT# | Blend composition | | Load/ g | Time/ s | Thickness/ mm | drilling coefficient |
|---|---|---|---|---|---|---|---|
| 1 | A090203-1 | PP/W/TiO2 | 55/40/5 | 300 | 12.8 | 3.025 | 4.57 |
| 2 | A090203-2 | PP/PI/W/TiO$_2$ | 27.5/27.5/40/5 | 100 | 18.8 | 3.075 | 2.12 |
| 3 | A090202-2 | PP/PI/ZnO | 15/15/70 | 200 | 8.6 | 3.125 | 6.17 |
| 4* | A090202-1 | PP/ZnO | 30/70 | 200 | 43.6 | 3.100 | 8.75 |
| 5 | A090202-3 | Tecothane/ZnO | 30/70 | 200 | 18.5 | 3.250 | −0.79 |
| 6 | A090202-5 | Tecothane/W/TiO2 | 55/40/5 | 200 | 31.3 | 3.225 | −0.34 |
| 7 | A090202-4 | Carbothane/BiOCl | 55/45 | 400 | 16.5 | 3.300 | −0.47 |
| 8 | A090202-6 | Tecoplast TP-470/W/TiO$_2$ | 55/40/5 | 500 | 60 | 3.225 | −0.84 |
| 9 | A090317-1 | Carbothane/W/TiO2 | 55/40/5 | 200 | 14.1 | 3.375 | 3.12 |
| 10 | A081029-6 | FEP/W | 60/40 | 300 | 25.2 | 3.196 | 0.88 |
| 11 | A081029-5 | Tefzel ®/W | 60/40 | 500 | 51.5 | 3.215 | −0.90 |

*Reference Example

Comparative Example 1

Preparation of a Polymer Blend Composed of an Epoxide-Amine Addition Polymer, Vectra and Tungsten According to EP 1 911 433

1. Epoxide-Amine Addition Polymer 72.183 g (0.212 mol) N,N'-Dibenzyl-5-oxanonandiamin-1,9, 32.274 g (0.212 mol) 1-amino-adamantane and 145.544 g (0.424 mol) Bis-2,2-[4-(2,3-epoxypropoxy)-phenyl]-propane were polymerized for 120 hours at 50° C. The resulting epoxide-amine addition polymer is soluble in organic solvents like THF, CHCl$_3$ and CHCl$_3$/CH$_3$OH.

2. Polymer Blend 250 g of the epoxide-amine addition polymer, 1050 g VECTRA™ A-950 and 1400 g tungsten powder were blended with an extruder in the temperature range of 280-310° C.

The obtained thermoplastic composite material was used for injection molding to form root canal cones and cylindrical rods having a flexural strength of 150.3±7.3 MPa and a drilling coefficient D=19 g s$^2$ mm$^{-2}$.

| | Load g | Time s | Thickness mm | D g s$^2$ mm$^{-2}$ |
|---|---|---|---|---|
| Comparative Example 1 | 500 | 20 | 2 | 50000 |
| Gutta-Percha (GP) | 100 | 10 | 2 | 2500 |
| Drilling coefficient D | | | | 19 |

Comparative Example 2

Preparation of an Epoxide-Amine Addition Polymer According to EP 1 843 714

128.313 g (337.67 mmol) bisphenol-A diglycidyl ether (M$_n$ 380 g/mol), 10.535 g (33.77 mmol) bisphenol-F diglycidyl ether, 28.140 g (185.72 mmol) 1-amino-adamantane, 63.241 g (185.72 mmol) N,N'-dibenzyl-5-oxanonanediamine-1,9 and 660.070 g CaWO$_4$, 165.018 g ZrO$_2$, and 9.980 g Aerosil 200 were mixed homogeneously and polymerized 24 hours at 60° C.

The composition is characterized by following values: radio-opacity RO=10.1 mm/mm Al glass transition temperature Tg=64° C. and volumetric shrinkage 1.13 vol.-%.

The obtained thermoplastic composite material was used for injection molding to form root canal cones and cylindrical rods having a flexural strength of 44±3 MPa and a drilling coefficient D=19 g s$^2$ mm$^{-2}$.

| | Load g | Time s | Thickness mm | D g s$^2$ mm$^{-2}$ |
|---|---|---|---|---|
| Comparative Example 2 | 500 | 20 | 2 | 50000 |
| Gutta-Percha (GP) | 100 | 10 | 2 | 2500 |
| Drilling coefficient D | | | | 19 |

Example 2

Endodontic root canal filling points of the size Taper 02/40 (ISO 6877:2006) were injection molded using a polymer blend composed of 55 wt.-% Tecothane TT-1075D (Lubrizol), 40 wt.-% Tungsten and 5 wt.-% Titanium dioxide. The points show after storage for 5 days at 37° C. and 90% relative humidity a change in the length of −1.644±0.029 mm and after 5 days at 50° C. a change in the length of −4.027±0.065 mm.

Comparative Example 3

Endodontic root canal filling points of the size Taper 02/40 (ISO 6877: 2006) were injection molded using a polymer blend composed of 55 wt.-% Carbothane PC3572D (Lubrizol), 40 wt.-% Tungsten and 5 wt.-% Titanium dioxide.

The points show after storage for 5 days at 37° C. and 90% relative humidity a change in the length of −7.062±0.135 mm and after 5 days at 50° C. a change in the length of −8.340±0.024 mm.

The invention claimed is:

1. Dental obturator point having an obturation body containing a composite material comprising
   (a) a polymer wherein the polymer is a polyurethane comprising the following repeating units:

—[NHCOOR$^1$OCONR$^2$]$_n$— wherein R¹ represents a straight or branched C1-C8 alkylene group and R² represents an aromatic moiety; and
(b) a particulate filler,
whereby the obturation body has a radio opacity of at least 3 mm/mm Al, characterized in that the composite material has
(i) a tensile strength of from 5 to 70 MPa,
(ii) a flexural strength of from 5 to 90 MPa,
(iii) a flexural module of from 0.1 to 2.5 GPa, and which has
(iv) a 300 rpm drilling coefficient at 37° C. in the range of from −1 to 7.00.

2. The dental obturator point according to claim 1, wherein the dental obturator point has a dimensional stability in the longitudinal direction of not more than 0.25% per mm total length of the obturator point after storage for 5 days at 37° C. and 90% relative humidity.

3. The dental obturator point according to claim 1, wherein the composite material comprises 80 to 20 percent by weight of the polymer based on the total weight of the composite material.

4. The dental obturator point according to claim 1, wherein the composite material comprises 20 to 80 percent by weight of the particulate filler based on the total weight of the composite material.

5. The dental obturator point according to claim 1, wherein the filler is selected from the group consisting of tungsten, barium tungstenate, calcium tungstenate, bismuth oxide, aluminium oxide, bismuth oxychloride, barium oxide, barium sulfate, strontium oxide, tungsten oxide, zinc oxide, zirconium oxide, ytterbium, yttrium, lanthanum carbonate and zirconium carbonate.

6. The dental obturator point according to claim 1, obtained by molding said composite material.

7. The dental obturator point according to claim 1, which comprises a tapered obturating point portion integrally connected at a distal end of a functional portion, whereby the functional portion comprises
(a) a neck portion adjacent to the obturating point portion, and
(b) a handle portion.

8. A method for producing a dental obturator point, which comprises the following steps:
(1) providing a thermoplastic composite material comprising a polymer and a particulate filler, wherein the polymer is a polyurethane comprising the following repeating units:

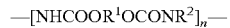

wherein R¹ represents a straight or branched C1-C8 alkylene group and R² represents an aromatic moiety, and
(2) molding the composite material to provide a dental obturator point having an obturation body having a radio opacity of at least 3 mm/mm Al,
characterized in that the composite material has
(i) a tensile strength of from 5 to 70 MPa,
(ii) a flexural strength of from 5 to 90 MPa,
(iii) a flexural module of from 0.1 to 2.5 GPa, and which has
(iv) a 300 rpm drilling coefficient at 37° C. in the range of from −1 to 7.00.

9. The method according to claim 8, wherein the composite material comprises 80 to 20 percent by weight of the polymer based on the total weight of the composite material.

10. The method according to claim 8, wherein the composite material comprises 20 to 80 percent by weight of the particulate filler based on the total weight of the composite material.

11. The method according to claim 8, wherein the filler is selected from the group consisting of tungsten, barium tungstenate, calcium tungstenate, bismuth oxide, aluminium oxide, bismuth oxychloride, barium oxide, barium sulfate, strontium oxide, tungsten oxide, zinc oxide, zirconium oxide, ytterbium, yttrium, lanthanum carbonate and zirconium carbonate.

12. The method according to claim 8, wherein the step of molding comprises injection molding.

* * * * *